United States Patent [19]

Voelter

[11] Patent Number: 4,772,721
[45] Date of Patent: Sep. 20, 1988

[54] N$^\tau$-SUBSTITUTED HISTIDINE DERIVATIVES

[75] Inventor: Wolfgang Voelter, Tubingen, Fed. Rep. of Germany

[73] Assignee: Diamalt AG, Fed. Rep. of Germany

[21] Appl. No.: 622,595

[22] Filed: Jun. 20, 1984

[51] Int. Cl.$^4$ ........................................... C07D 233/64
[52] U.S. Cl. .................................... 538/342; 548/344
[58] Field of Search ............................... 548/342, 344

[56] References Cited

PUBLICATIONS

Pyman, Chem Abst. 6, 1149$^8$ (1912).
Plow, Chem Abst. 88, 17640y (1978).
Climie et al., Tetrahedron, 38(s), pp. 697–711 (1982).
Heinrikson et al., J. Biol. Chem., 240 (7), pp. 2921–2934 (1965).
Noordam et al., Recl. Trav. Chim. Pays-Bas, 97(11) pp. 293–295 (1978).
Shenoy et al., Amer, Dye. Rept., May 6, 1968, pp. 352–369 (1968).

Primary Examiner—Mary C. Lee
Assistant Examiner—Kurt G. Briscoe

Attorney, Agent, or Firm—Millen & White

[57] ABSTRACT

A process is disclosed for the preparation of new N$^\tau$-substituted histidine derivatives of the general formula

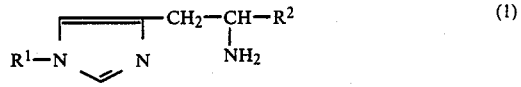

According to the process, a histidine derivative of the general formula

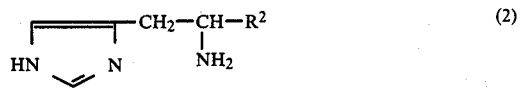

is reacted with phosgene, and the resultant product is then alkylated and thereafter hydrolyzed with an acid.

The products obtained by the process are highly useful for preparation of histidine-analogous proteins and enzymes.

4 Claims, No Drawings

$N^\tau$-SUBSTITUTED HISTIDINE DERIVATIVES

BACKGROUND OF THE INVENTION

The invention concerns a process for the preparation of $N^\tau$-substituted histidine derivatives, $N^\tau$-substituted histidine derivatives, and the use thereof for the preparation of peptide derivatives, especially highly active hormone derivatives and enzyme derivatives.

Relatively early, proof was obtained of the existence of the two isomeric amino acids 1-methylhistidine of Formula 6 below and 3-methylhistidine of Formula 7 below, according to IUPAC nomenclature $N^\pi$-(pros)- and $N^\tau$-(tele)methylhistidine:

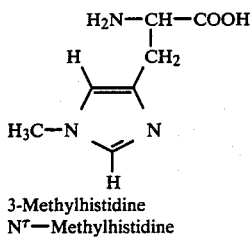

3-Methylhistidine
$N^\tau$—Methylhistidine

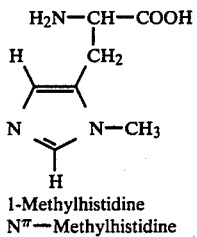

1-Methylhistidine
$N^\pi$—Methylhistidine $N^\pi$-Methylhistidine was recognized as early as 1938 as a component of anserine, a dipeptide of the structure β-alanyl-L-$N^\pi$-methylhistidine, which was proven to exist in meat extracts.

The free amino acid $N^\pi$-methylhistidine was isolated—just as the $N^\tau$-methyl compound—for the first time from urine. The compound isomeric with respect to anserine, namely β-Ala-L-$N^\tau$-methyl-His, could be isolated from whale meat.

The amino acid $N^\tau$-methylhistidine is a component of the myofibrillar proteins actin and myosin which contain practically all of the 3-methylhistidine formed in the body. Methylation takes place only after incorporation of histidine into the respective peptide chain.

Various reports can be found in the literature regarding experiments for the production of $N^\tau$- and $N^\pi$-alkylated histidine derivatives. Attempts have been made to introduce the correspondingly substituted nitrogen during the course of a total synthesis of the molecule. This has been tried repeatedly for the $N^\tau$-histidines [H. H. Tallan, W. H. Stein, and S. Moore, J. Biol. Chem. 206 : 825 (1954); H. Rinderknecht, T. Rebane, and V. Ma, J. Org. Chem. 293 : 1968 (1964); P. K. Martin, H. R. Matthews, H. Rapoport, and G. Thyagarajan, J. Org. Chem. 33 : 3758 (1968)]. However, the efforts failed due to a non-stereo-specific course of the reactions and/or due to lack of a suitable separating method for the thus-obtained racemic mixtures.

Furthermore, attempts have been made to obtain the two isomeric alkyl compounds by direct alkylation of histidine and suitable derivatives. Using the customary alkylation processes, inseparable mixtures of the two isomers were produced in low yields.

SUMMARY OF THE INVENTION

It is an object of the present invetnion, therefore, to provide a practicable synthesis method for the preparation of $N^\tau$-substituted histidine derivatives, especially optically pure $N^\tau$-substituted histidine derivatives.

It is another object to provide novel $N^\tau$-substituted histidine derivatives per se along with uses thereof for the production of protein derivatives and enzyme derivatives, such as polypeptide and peptide analogs, and especially for the production of highly active hormone derivatives.

It is yet another object to provide such a process employing methods of classical peptide synthesis and, if at all possible, which avoids expensive purifying steps during the course of the synthesis.

It is a further object to provide a synthesis optimized with respect to yield, duration, and the use of blocking groups.

Upon further study of the specification and appended claims, further objects and advantages of this invention will become apparent to those skilled in the art.

These objects have been attained by this invention by providing a process for the production of $N\tau$-substituted histidine derivatives of Formula 1

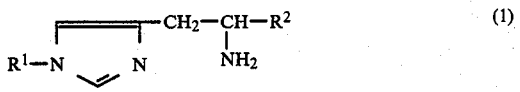

wherein
$R^1$ is $C_1$-$C_6$-alkyl, $C_3$-$C_6$-cycloalkyl, $C_1$-$C_6$-ω-haloalkyl or or $C_1$-$C_6$-ω-aminoalkyl, all of which can be substituted by cyano, nitro, $C_1$-$C_3$-alkoxy, or —$COOC_nH_{2n+1}$ (wherein n is 1 to 3); $C_2$-$C_6$-alkenyl; $C_3$-$C_6$-cycloalkenyl; or $C_1$-$C_6$-alkylenearyl,
$R^2$ is hydrogen, $C_1$-$C_6$-alkyl, or —$COOR^3$, wherein
$R^3$ is hydrogen, amino, or $C_1$-$C_6$-alkyl,
comprising reacting a histidine derivative of Formula 2 below, wherein $R^2$ is as defined for Formula 1, with phosgene under conditions which form the intermediate product of Formula 3 according to the following equation

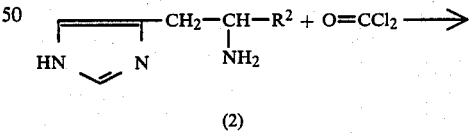

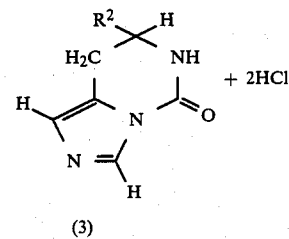

in the presence of an organic solvent, at a temperature in the range from $-10°$ C. to $-50°$ C. and in the presence of an agent for binding the acid;

alkylating the resultant product with an excess of an alkyl halogenide of Formula 4. The term "alkyl halogenide" is used since the halogen atom is attached to the portion of all $R^1$ groups which is an alkyl-based portion or in the case of alkenyl or cycloalkenyl, where there is no alkyl portion, a vinyl carbon atom. In all cases, the reaction will proceed with the resultant compound $R^1$-hal.

$$R^1-Hal \quad (4)$$

wherein
$R^1$ is as defined above and
Hal is a halogen atom,
thereby forming a (7S)- 5,6,7,8-tetrahydro-7-$R^2$-2-$R^1$-subst.-5-oxoimidazopyrimidinium halogenide of Formula 5

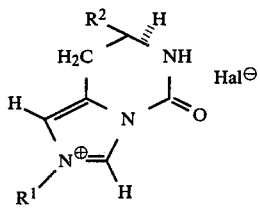

wherein
$R^1$ and $R^2$ are as defined above and
Hal is a halogen atom;
hydrolyzing the product of Formula 5 to form the corresponding N$^\tau$-substituted histidine of Formula 1 by treatment with an acid, and
isolating the product from teh reaction mixture.

Furthermore, in another aspect, these objects have been attained by this invention by providing N$^\tau$-substituted histidine derivatives of Formula 1

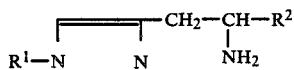

wherein
$R^1$ is $C_1-C_6$-alkyl, $C_3-C_6$-cycloalkyl, $C_1-C_6$-$\omega$-haloalkyl, $C_1-C_6$-$\omega$-aminoalkyl, any of the foregoing groups substituted by cyano, nitro, $C_1-C_3$-alkoxy, or —COOC$_n$H$_{2n+1}$ (wherein n is 1 to 3); $C_1-C_6$-alkenyl; $C_3-C_6$-cycloalkenyl; or $C_1-C_6$-alkylene aryl;
$R^2$ is hydrogen $C_1-C_6$-alkyl, or —COOR$^3$ wherein $R^3$ is hydrogen, amino, or $C_1-C_6$-alkyl, with the proviso that when $R^1$ is methyl or ethyl, $R^2$ is not carboxy.

These objects have been attained in yet another aspect by providing a use of the N$^\tau$-substituted histidine derivatives according to this invention for the production of histidine-analogous protein derivatives and enzyme derivatives, especially for the production of peptide or polypeptide derivatives, expecially preferably for the production of histidine-analogous gonadoliberin derivatives.

DETAILED DISCUSSION

In the above Formulae 1, 4 and 5, $R^1$ can be a $C_1-C_6$-alkyl group. The alkyl group can be linear or branched; examples include methyl, ethyl, n-propyl, isopropyl, n-butyl, isobutyl, and tert-butyl. Among these groups, methyl and the tertiary and secondary butyl groups are especially preferred. $R^1$ can furthermore be $C_3-C_6$-cycloalkyl, e.g., a cyclopropyl or cyclopentyl group;

$C_1-C_6$-$\omega$-haloalkyl or $C_1-C_6$-$\omega$-aminoalkyl. Preferred $\omega$-substituted alkyl groups are the aforementioned alkyl groups substituted in the $\omega$-position by a halogen, for example, chlorine, fluorine, bromine, or iodine, or substituted in the $\omega$-position by an amino group.

These aforementioned $R^1$ groups can be unsubstituted or further substituted by the above-recited substituents. These are —CN, —NO$_2$, $C_{1-3}$-alkoxy or —COOC$_n$H$_{2n+1}$, in each case the alkyl portions being, e.g., methoxy, ethoxy, n-propoxy, or iso-propoxy. Usually, 1-2 substituents will be present when the groups are substituted, preferably one substituent.

Other $R^1$ groups are $C_{2-6}$-alkenyl, e.g., vinyl, allyl, 1-, 2- or 3-butenyl, 1-, 2-, 3-, 4-, or 5-hexenyl, etc., the alkyl portions being straight chained or branched; $C_{3-6}$-cycloalkenyl, e.g., cyclopropenyl, 1- or 2-cyclobutenyl, 1-, 2- or 3-cyclohexenyl, etc.; (for all of these unsaturated groups, one double bond is preferred, but more than one can exist where possible, e.g., 1-3 double bonds); and $C_{6-10}$-aryl-$C_{1-6}$-alkylene. In the latter group, the aryl group can be phenyl or 1- or 2-naphthyl. The alkylene portion can be linear or branched, e.g., methylene, propylene, hexylene, 3-methylpentylene, etc. The aromatic groups can furthermore be substituted by one to three substituents, e.g., $C_1-C_3$-alkyl, halogen (fluorine, bromine, chlorine, or iodine), trifluoromethyl, nitro, cyano, or —COO—$C_1-C_3$-alkyl.

Among the meanings given above for $R^1$, a linear or branched $C_1-C_6$-alkyl group or a linear or branched $C_1-C_6$-alkylene aryl group is preferred. Particularly preferably, $R^1$ is a methyl, ethyl, or benzyl group.

In the above formulae, $R^2$ is hydrogen or linear or branched $C_1-C_6$-alkyl, for example, methyl, ethyl, n-propyl, isopropyl, n-butyl, isobutyl, tert-butyl, etc. $R^2$ can furthermore be —COOR$^3$ wherein $R^3$ is hydrogen, amino, or $C_1-C_6$-alkyl. When $R^3$ is $C_1-C_6$-alkyl, this group can be linear or branched, as exemplified agove. Preferably, $R^2$ is hydrogen or $C_1-C_3$-alkyl, and especially preferably is hydrogen.

It has been surprisingly found that a very stable, fully reversible blockage of the N$^\tau$-function of the imidazole residue on the histidine molecule is possible by reacting the histidine derivatives with phosgene in the presence of a base at low temperatures. The following equation illustrates the course of the reaction, using the methyl ester of histidine.

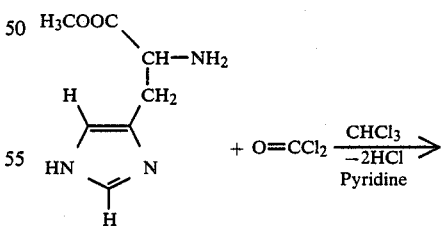

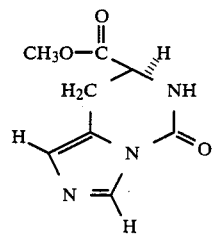

Preparation of
(7S)-5,6,7,8-Tetrahydro-7-methoxycarbonyl-5-oxoimidazo[1,5-c]pyrimidine Essentially the same reaction conditions as discussed above and below with respect to specific values of $R^2$ will also be suitable for all other embodiments of $R^2$.

In the first stage of the process, the above-listed compounds of Formula 2 are used as the starting material. Reaction of the compounds of Formula 2 with phosgene takes place in an organic solvent inert with respect to phosgene and still liquid at the reaction temperature or, together with the other reactants, forming a liquid mixture. Examples of suitable solvents include hydrocarbons, halogenated hydrocarbons, such as methylene chloride, chloroform, tetrachloroethane, trichloroethane, ethers, such as dioxane, diethyl ether, tetrahydrofuran, or dipolar aprotic solvents, such as dimethylformamide, dimethyl sulfoxide, or hexamethylphosphoric triamide. Hydrocarbons and ethers are preferred. The reaction is carried out at temperatures in the range from $-10°$ C. to $-50°$ C., preferably $-20°$ C. to $-40°$ C., especially preferably at about $-35°$ C. The molar ratio of phosgene to compounds of Formula 1 usually is 1 : 1 to 10 : 1.

An agent for binding the hydrochloric acid formed is utilized during the reaction. Agents for binding the hydrochloric acid include the usual bases. Pyridine, triethylamine, or trimethylamine is preferably employed. The amount thereof is usually a slight excess of the stoichiometric amount.

In general, the phosgene is introduced into the solution at the desired temperature, for example by cooling in a methanol/dry ice bath, and then the mixture is stirred with cooling for a period of 10–60 minutes. The resultant reaction mixture is thereafter poured into a cooled agent which is not a solvent for the reaction product, for example, ether, hexane, etc.

In general, a fine, white, readily deliquescent precipitate of the reaction product of Formula 3 is then precipitated. The precipitate is suctioned off and washed with the solvents with which it was precipitated. For example, compound 3 wherein $R^2$ is a methoxy group can be crystallized from methanol in beautiful crystals and with high purity. The compound is stable at room temperature and under the effect of light, and no decomposition is observed in the course of two years.

Alkylation at the $N^\tau$-atom of the imidazole residue of 5,6,7,8-tetrahydro-7-alkoxycarbonyl-5-oxoimidazole1,5,10-pyrimidine of Formula 3 is readily accomplished with high yields, by reacting the compound with an excess of alkyl halogenide of Formula 4.

Preferably, a tenfold excess of freshly distilled alkyl halogenide is utilized, such as, for example, the iodide or chloride or bromide. Thus, the iodides or bromides can be utilized as the alkylating agents, for example. The iodides are employed with preference. Examples of alkylating agents are methyl, ethyl, n-propyl, isopropyl, and n-butyl iodide or other halide.

In general, the compound of Formula 3 is heated with the excess of alkyl halogenide under reflux. The thus-produced alkyl pyrimidinium halogenides are generally crystallized after adding an organic nonpolar solvent, e.g., methylene chloride, chloroform, halogenated hydrocarbons.

Liberation of the histidine derivatives alkylated in the $N^\tau$-position is readily achieved and in almost quantitative yield by boiling with a mineral acid. Generally, strong acids are used as the mineral acids, e.g., hydrochloric acid, sulfuric acid, or perchloric acid. The concentration of the acid is, in general, 4N to 8N, preferably 6N. However, it is also possible to utilize concentrations lying below the above-indicated range.

The $N^\tau$-alkyl histidine derivatives are preferably crystallized from ethanol as the dihydrochlorides after the addition of ether.

The compounds are stable and not light-sensitive at room temperature. However, if the free base is liberated and maintained in solution at room temperature, then decomposition takes place with the solution assuming a brown color, as is also observed in case of the free histidine methyl ester.

By using a racemate as the starting material in the process of this invention, a racemic mixture is likewise obtained as the end product. This racemic mixture can be separated by conventional methods. If the pure L- or pure D-compounds are employed in the process of the invention, then the pure L- and pure D-compounds, respectively, are obtained as well. The process of this invention, therefore, provides synthesis of optically pure compounds in a simple way.

All starting materials of Formula 2 and Formula 4 are either known or readily preparable using fully conventional methods starting from known or readily conventionally preparable starting materials.

It has furthermore been found that the newly synthesized $N^\tau$-substituted histidine derivatives of Formula 1 can be utilized for the production of biologically important compounds, so-called biomolecules.

The compounds of this invention can be employed for the synthesis of histidine-analogous peptide or polypeptide derivatives, i.e., proteins and enzymes wherein the usual histidine component is replaced by a histidine component of this invention. They are preferably utilized for the preparation of protein or enzyme derivatives, especially preferably for the preparation of histidine-analogous gonadoliberin derivatives. It was found that, for example, the TRH-releasing activity of tripeptides containing, in place of histidine, a $N^\tau$-methylhistidine derivative, is significantly higher than that of the histidine-containing tripeptides, as can be seen from the following table.

TABLE

| Compound | Activity Based on TRH = 100% | |
|---|---|---|
| L-Pyr—1-Me—L-His—L-Pro—NH$_2$ | 0.1 | |
| L-Pyr—1-Me—L-His—L-Pro—NH$_2$ | 0.04 | |
| L-Pyr—1-Me—L-His—L-Pro—NH$_2$ | 0.04 | |
| L-Pyr—3-Me—L-His—L-Pro—NH$_2$ | 800 | THIS |
| L-Pyr—3-Me—L-His—L-Pro—NH$_2$ | 800 | INVENTION |
| L-Pyr—3-Me—L-His—L-Pro—NH$_2$ | 800 | |

All of the histidine-analogous peptides or polypeptides, e.g., proteins or enzymes, which are preparable in accordance with this invention, will be useful for the same purposes as the prior art histidine-analogous compounds, e.g., for the same purposes as the natural histidine compounds. Furthermore, all of the compounds preparable by the process of this invention can be used as nutrients in media used to culture microorganisms, e.g., bacteria.

The compounds of this invention can be utilized in conventional processes for the synthesis of all biomolecules containing histidine in order to prepare the analogs of this invention, for example for the synthesis of hypothalamic hormones. For example, all of the methods recited in Derek Gupta and Wolfgang Voelter, Proceedings of the European Colloquium on Hypothalamic Hormones, held at Tubingen (West Germany) in February 1974, Publishers: Chemie, can also be conducted with the compounds of this invention.

The following description depicts the use of $N^\tau$-alkylated histidine derivatives for the preparation of histidine-analogous gonadoliberin derivatives.

The model compound chosen for a peptide synthesis using the alkyl histidines prepared according to this invention was gonadotropin-releasing hormone (GnRH, LH/FSH-RH). Since its isolation and structural clarification, this decapeptide, formed in the hypothalamus and effecting in the hypophysis the release of the gonadotropic hormones, has been the subject of intensive chemical and medical research.

The abbreviations set out below are utilized in the specification and in the examples below:

| | |
|---|---|
| Adpoc = | 1-(1-Adamantyl)-1-methylethoxycarbonyl |
| Boc = | tert-Butoxycarbonyl |
| Bzl = | Benzyl ether |
| DCC = | N,N'—Dicyclohexylcarbodiimide |
| DMF = | Dimethylformamide |
| EE = | Ethyl acetate |
| EtOH = | Ethanol |
| Et = | Ethyl |
| FD-MS = | Field desorption mass spectrometry |
| HOBt = | 1-Hydroxybenzotriazole |
| HAc = | Acetic acid |
| Mbs = | p-Methoxybenzenesulfonyl |
| Me = | Methyl |
| MeOH = | Methanol |
| OMe = | Methyl ester |
| OBzl = | Benzyl ester |
| PFT = | Pulse Fourier transformation |
| OSu = | N—Hydroxysuccinimide ester |
| THF = | Tetrahydrofuran |
| Z = | Benzyloxycarbonyl |

Without further elaboration, it is believed that one skilled in the art can, using the preceding description, utilize the present invention to its fullest extent. The following preferrred specific embodiments are, therfore, to be construed as merely illustrative, and not limitative of the remainder of the disclosure in any way whatsoever. In the following examples, all temperatures are set forth uncorrected in degress Celsius; unless otherwise indicated all parts nad percentages are by weight.

EXAMPLE 1

(1) L-Histidine Methyl Ester . 2 Hydrochloride (H-L-His-OMe . 2HCl)

The compound is prepared according to N. C. Davis, J. Biol. Chem. 223 : 935 (1956).

[Charge: 60 g (0.31 mol) L-histidine hydrochloride.]

Deviating from the directions, the mixture is heated under reflux until a clear solution has been formed. Then, dry gaseous hydrogen chloride is introduced for 2 hours.

Yield: 64 g (85% of theory).
mp: 198°–200° C., lit. 200°–201° C.

(2) L-Histidine Methyl Ester (H-L-His-OMe)

In a mortar, 12.1 g (0.05 mol) of crystalline L-histidine methyl ester dihydrochloride is finely triturated and suspended in 150 ml of absolute chloroform. Under ice cooling, dry ammonia gas is then introduced for 10 minutes and the thus-precipitated ammonium chloride is filtered off. The clear chloroform phase is concentrated to dryness under vacuum. The free methyl ester, obtained as a colorless oil, is stored in a cool, dark environment.

Yield: 8.45 g (quantitative).

The compound is reacted without further characterization.

(3) (+)-(S)-5,6,7,8-Tetrahydro-7-(methoxycarbonyl)-5-oxoimidazo[1,5-c]pyrimidine 3.38 g (20 mmol) of L-histidine methyl ester and 3.16 g (40 mmol) of pyridine (distilled over ninhydrin) are dissolved in 100 ml of chloroform and cooled with methanol/dry ice to −30° to −40° C. At this temperature, a weak stream of HCl-free phosgene is introduced for 15 minutes and the mixture is stirred for 15 minutes in the cold state. Then the batch is poured into 400 ml of cold ether/hexane (2:1). A fine, white, readily deliquescent precipitate is obtained which is suctioned off and washed with ether. The precipitate is taken up in 200 ml of 1N sodium bicarbonate solution and extracted six times with respectively 50 ml of chloroform. The CHCl$_3$ phase is dried over sodium sulfate and concentrated under vacuum. Remaining traces of pyridine are removed under a high vacuum. The compound is crystallized from methanol in beautiful, colorless crystals.

Yield: 3.39 g (87% of theory).
mp: 160°–162° C.

(4) (+)-(S)-2-Methyl-5,6,7,8-tetrahydro-7-(methoxycarbonyl)-5-oxoimidazo[1,5-c]pyrimidine Hydroiodide 3 g (15.3 mmol) of the 5,6,7,8-tetrahydro-7-(methoxycarbonyl)-5-oxoimidazopyrimidine is dissolved in 30 ml of absolute dimethylformamide and combined with 9.34 ml (150 mmol) of freshly distilled methyl iodide. The mixture is refluxed for 2.5 hours, allowed to cool down to room temperature, and poured into 150 ml of ether. The crystalline compound is suctioned off, washed with a small amount of cold methanol and ether, and recrystallized from methanol. The compound should be stored under exclusion of light and in a cold environment.

Yield: 4.7 g (91% of theory).
mp: 171°–172° C.

(5) L-N$^\tau$-Methylhistidine .2 Hydrochloride (H-L-His(N$^\tau$-Me)OH.2 HCl)

3.37 g (10 mmol) of (+)-(7S)-5,6,7,8-tetra-hydro-7-(methoxycarbonyl)-2-methyl-5-oxoimidazo[1,5-c]pyrimidine hydroiodide is heated under reflux in 40 ml of 6N HCl until no starting compound can be detected any longer by thin-layer chromatography (6-8 hours). Then, the hydrochloric acid is withdrawn under vacuum, the oily residue is taken up in ethanol and crystallized by addition of ether.

Yield: 2.0 g (83% of theory).
mp: 258° C.

EXAMPLE 2

(1) (+)-(7S)-2-Ethyl-5,6,7,8-tetrahydro-7-(methoxycarbonyl)-5-oxoimidazo[1,5-c]pyrimidine Hydroiodide 3.9 g (20 mmol) of the (7S)-5,6,7,8-tetrahydro-7-(methoxycarbonyl)-5-oxoimidazopyrimidine is heated under reflux with 31.1 g (200 mmol) of freshly distilled ethyl iodide, obtained according to Example 1, and 40 ml of absolute dimethylformamide for 3 hours. The mixture is then allowed to cool down to room temperature, and ether is added until turbidity occurs. The product is obtained at 4° C. in the form of yellow crystals and is recrystallized from methanol The compound should be stored in a dark and cool environment since dark discoloration and decomposition occur under light.

Yield: 6.24 g (89% of theory).
mp: 140° C. (decomposition).

(2) L-$N^\tau$-Ethylhistidine . 2 Hydrochloride
(H-L-His($N^\tau$-Et)-OH . 2HCl)

1.75 g (5 mmol) of the (+)-(7S)-2-ethyl-5,6,7,8-tetrahydro-7-(methoxycarbonyl)-5-oxoimidazopyrimidine hydroiodide, prepared according to the above directions, is heated under reflux in 20 ml of 6N hydrochloric acid for 6 hours. The hydrochloric acid is then entirely removed under a high vacuum, the red-colored, oily residue is taken up in ethanol, dried, and crystallized by addition of ether.

Yield: 0.97 g (76% of theory).
mp: 235° C.

EXAMPLE 3

(1)
(−)-(R)-5,6,7,8-Tetrahydro-7-methoxycarbonyl-5-oxoimidazo[1,5-c]pyrimidine 1.7 g (10 mmol) of D-histidine methyl ester and 1.58 g (20 mmol, 1.61 ml) of distilled pyridine are dissolved in 50 ml of absolute chloroform, cooled to −40° to −50° C. with methanol/dry ice, and, at this temperature, a weak stream of HCl-free phosgene is introduced for 15 minutes. The mixture is stirred for 15 minutes in the cold state and poured into 200 ml of cold ether/hexane (2:1). A white, deliquescent precipitate is obtained which is quickly suctioned off and washed with ether. The precipitate is taken up in 100 ml of 1N Na$_2$CO$_3$ solution and extracted six times with chloroform. After drying of the organic phase over sodium sulfate, the solvent is removed by evaporation; any present traces of pyridine are removed under a high vacuum. The compound is crystallized from methanol.

Yield: 1.45 g (85% of theory).
mp: 164° C.

EXAMPLE 4

Peptide Synthesis Using $N^\tau$-Alkyl Histidines (1)
N-Benzyloxycarbonyl-L-pyroglutamyl-$N^\tau$-methyl-L-histidine (Z-L-Pyr-L-His($N^\tau$-Me)-OH)

1.48 g (4.11 mmol) of Z-L-Pyr-OSu is dissolved in 5 ml of dioxane and combined with a solution of 0.69 g (4.11 mmol) of H-L-His($N^\tau$-Me)-OH and 0.43 g (4.1 mmol) of anhydrous sodium carbonate in 5 ml of water. The mixture is agitated for 4 hours at room temperature and then neutralized with 0.1N hydrochloric acid. The solvent is removed under a high vacuum, the residue is taken up in a small quantity of methanol, and the undissolved sodium chloride is filtered off. Since crystallization from 30% methanol (as in case of the non-alkylated compound) is unsuccessful, the product is obtained by reprecipitating twice from methanol/ether.

Yield: 1.05 g (62%).
mp: 144° C.

(2)
N-Benzyloxycarbonyl-L-pyroglutamyl-$N^\tau$-ethyl-L-histidine (Z-L-Pyr-L-His($N^\tau$-Et)-OH)

0.72 g (2 mmol) of Z-L-Pyr-OSu is dissolved in 4 ml of dioxane and combined with a solution of 0.36 g (2 mmol) of H-L-His($N^\tau$-Et)-OH and 0.21 g (2 mmol) of anhydrous sodium carbonate in 3 ml of water. The mixture is stirred for 6 hours at room temperature. After termination of the reaction, the mixture is neutralized with 0.1N hydrochloric acid, and the batch is evaporated to dryness under a high vacuum. The remaining oil is taken up in a small amount of methanol, the undissolved sodium chloride is filtered off, and the product is obtained by reprecipitation from methanol/ether. Yield: 490 mg (58%); mp: 156°–158° C.

(3)
N-Benzyloxycarbonyl-L-pyroglutamyl-$N^\tau$-methyl-L-histidyl-L-prolinamide
(Z-L-Pyr-L-His($N^\tau$-Me)-L-Pro-NH$_2$)

414 mg (1 mmol) of Z-L-Pyr-L-His($N^\tau$-Me)-OH, 220 mg (1.1 mmol) of dicyclohexylcarbodiimide, and 135 mg (1 mmol) of 1-hydroxybenzotriazole are dissolved in 10 ml of DMF and combined at 0° C. with a solution of 150 mg (1 mmol) of L-Pro-NH$_2$.HCl and 100 mg (1 mmol) of N-methylmorpholine in a small amount of DMF. The mixture is stirred for one hour at 0° C. and overnight at room temperature. Thereafter, the mixture is filtered off from precipitated dicyclohexylurea under cold conditions, the solvent is withdrawn under a high vacuum, and the residue is taken up in ethyl acetate, washed with bicarbonate and water, dried over sodium sulfate, and the product is precipitated from ethyl acetate/methanol (9:1) by addition of ether.

Yield: 326 mg (64%).

(4)
L-Pyroglutamyl-$N^\tau$-methyl-L-histidyl-L-prolinamide
(H-L-Pyr-L-His($N^\tau$-Me)-L-Pro-NH$_2$)

255 mg (0.5 mmol) of blocked tripeptide is dissolved in 15 ml of methanol and 5 ml of water and combined with 50 mg of Pd/activated carbon (10% Pd). The mixture is hydrogenated for 2 hours at pH 4.5–5 (acetic acid) by the throughflow method. The activated carbon is filtered off through "Celite", the solvent is withdrawn, and the residue is taken up in water. The solution is combined with 1.5 g of ion exchanger (OH-form), allowed to stand for 20 minutes at room temperature, and filtered off.

The aqueous solution is freeze-dried.
Yield: 154 mg (82%).
Purification takes place by ion exchange chromatography on "Sephadex C-50".

(5)
N-Benzyloxycarbonyl-L-pyroglutamyl-$N^\tau$-ethyl-L-histidyl-L-prolinamide
(Z-L-Pyr-L-His($N^\tau$-Et)-L-Pro-NH$_2$)

215 mg (0.5 mmol) of Z-L-Pyr-L-His($N^\tau$-Et)-OH, 110 mg (0.55 mmol) of dicyclohexylcarbodiimide, and 70 mg (0.5 mmol) of 1-hydroxybenzotriazole are dissolved in 8 ml of dimethylformamide and cooled to 0° C. Then the mixture is combined with a solution of 75 mg (0.5 mmol) of L-Pro-NH$_2$.HCl and 50 mg (0.5 mmol) of N-methylmorpholine in a small amount of DMF, stirred for one hour under cold conditions and for 12 hours at room temperature. After removing the dicyclohexylurea by filtration, the solvent is removed under a high vacuum, and the residue is dissolved in ethyl acetate (by adding a few drops of methanol). The mixture is washed with sodium bicarbonate and water, dried, and the product is precipitated from ethyl acetate/methanol (9:1) by addition of ether.

Yield: 139 mg (53%).

(6) L-Pyroglutamyl-N$^\tau$-ethyl-L-histidyl-L-prolinamide (L-Pyr-L-His(N$^\tau$-Et)-L-Pro-NH$_2$)

104 mg (0.2 mmol) of the tripeptide, blocked with benzyloxycarbonyl, is dissolved in 10 ml of methanol and 5 ml of water and combined with 50 mg of Pd/activated carbon (10%). Hydrogenation is conducted for 2-3 hours by the throughflow method (pH 4.5 - 5, acetic acid), the catalyst is filtered off through "Celite", and the solvent is removed under vacuum. The residue is taken up in water, treated for 20 minutes with ion exchanger (OH-form), and then lyophilized.

Yield: 60 mg (76%).

EXAMPLE 5

Analogous to the methods described in Examples 1-4, the following compounds are also prepared:
3-propylhistidine
3-isopropylhistidine
3-butylhistidine
3-cyclopropylhistidine
3-cyclopentylhistidine
3-benzylhistidine.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. An N$^\tau$-substituted histidine of the formula

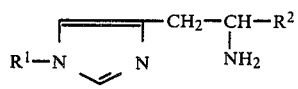

wherein
R$^1$ is C$_{1-6}$-alkyl substituted by nitro or C$_{1-3}$-alkoxy;
R$^2$ is hydrogen, C$_1$-C$_6$-alkyl, or —COOR$^3$; and
R$^3$ is hydrogen, amino, or C$_1$-C$_6$-alkyl.

2. A compound of claim 1 wherein R$^2$ is COOR$^3$ wherein R$^3$ is C$_{1-6}$-alkyl.

3. A compound of claim 1 wherein R$^2$ is H or alkyl.

4. An N$^\tau$-substituted histidine of the formula

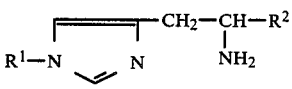

wherein
R$^1$ is C$_3$-C$_6$-cycloalkyl; C$_1$-C$_6$-$\omega$-haloalkyl; C$_1$-C$_6$-$\omega$-aminoalkyl; one of the foregoing substituted by cyano, nitro, C$_1$-C$_3$-alkoxy, or —COOC$_n$H$_{2n+1}$; C$_2$-C$_6$-alkenyl; C$_3$-C$_6$-cycloalkenyl; or C$_1$-C$_6$-alkylene-C$_{6-10}$-aryl;
n is 1, 2 or 3;
R$^2$ is hydrogen, C$_1$-C$_6$-alkyl, or —COOR$_3$; and
R$^3$ is hydrogen, amino, or C$_1$-C$_6$-alkyl.

* * * * *